(12) United States Patent
Van Bommel et al.

(10) Patent No.: US 10,441,809 B2
(45) Date of Patent: Oct. 15, 2019

(54) TUNABLE WHITE LIGHT SOURCE WITH VARIABLE UV COMPONENT

(71) Applicant: SIGNIFY HOLDING B.V., Eindhoven (NL)

(72) Inventors: Ties Van Bommel, Eindhoven (NL); Rifat Ata Mustafa Hikmet, Eindhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 15/773,565

(22) PCT Filed: Oct. 25, 2016

(86) PCT No.: PCT/EP2016/075614
§ 371 (c)(1),
(2) Date: May 4, 2018

(87) PCT Pub. No.: WO2017/080807
PCT Pub. Date: May 18, 2017

(65) Prior Publication Data
US 2018/0318599 A1    Nov. 8, 2018

(30) Foreign Application Priority Data
Nov. 10, 2015 (EP) ..................................... 15193780

(51) Int. Cl.
*A61N 5/06* (2006.01)
*F21V 9/02* (2018.01)
(Continued)

(52) U.S. Cl.
CPC .............. *A61N 5/0613* (2013.01); *F21V 9/02* (2013.01); *H01L 33/50* (2013.01);
(Continued)

(58) Field of Classification Search
CPC .......... A61N 5/0613; F21V 9/02; H01L 33/50
See application file for complete search history.

(56) References Cited

U.S. PATENT DOCUMENTS

2005/0059362 A1    3/2005  Kalajo et al.
2010/0102736 A1    4/2010  Hessling
(Continued)

FOREIGN PATENT DOCUMENTS

DE    102005059362 A1    9/2006
JP    H08235903 A        9/1996
(Continued)

OTHER PUBLICATIONS

Ministry of Environment (Japan), "Ultraviolet Environmental Health Manual 2008", Rev. Edition Jun. 2008, pp. 11-13, http://www.env.go.jp/chemi/uv/uv_manual.html.

*Primary Examiner* — Thomas M Sember
(74) *Attorney, Agent, or Firm* — Daniel J. Piotrowski

(57) ABSTRACT

The invention provides a lighting system (10) comprising a first light source (100), a second light source (200) and a control system (20) configured to control the first light source (100) and the second light source (200), wherein: —the first light source (100) is configured to provide first light source light (101) comprising: (i) a UV component; and (ii) (iia) a blue component or (iib) a blue component and a yellow component; —the second light source (200) is configured to provide white second light source light (201) having a second light source light correlated color temperature (Tc2); —the lighting system (10) is configured to provide lighting system light (11) comprising one or more of said first light source light (101) and said second light source light (201), with the lighting system light (11) having a controllable correlated color temperature (Tc).

13 Claims, 3 Drawing Sheets

(51) Int. Cl.
   *H01L 33/50*     (2010.01)
   *F21Y 113/10*    (2016.01)
(52) U.S. Cl.
   CPC ............... *A61N 2005/0651* (2013.01); *A61N 2005/0661* (2013.01); *F21Y 2113/10* (2016.08)

(56) References Cited

U.S. PATENT DOCUMENTS

| | | |
|---|---|---|
| 2010/0287830 A1 | 11/2010 | Chen et al. |
| 2011/0037415 A1 | 2/2011 | Juestel et al. |
| 2012/0032208 A1 | 2/2012 | Brandes |
| 2013/0165741 A1 | 6/2013 | Seabury et al. |
| 2014/0160728 A1 | 6/2014 | Kim et al. |
| 2015/0014715 A1 | 1/2015 | Hsing Chen et al. |

FOREIGN PATENT DOCUMENTS

| | | | |
|---|---|---|---|
| JP | 2007103511 | A | 4/2007 |
| JP | 2009540599 | A | 11/2009 |
| JP | 2011023339 | A | 2/2011 |
| JP | 2013105746 | A | 5/2013 |
| JP | 2013105747 | A | 5/2013 |
| JP | 2015528210 | A | 9/2015 |
| WO | WO2008125672 | A1 | 10/2008 |
| WO | WO2010016009 | A1 | 2/2010 |
| WO | WO2010041717 | A1 | 4/2010 |
| WO | WO2012108065 | A1 | 8/2012 |
| WO | WO2012144087 | A1 | 10/2012 |
| WO | WO2013061942 | A1 | 5/2013 |
| WO | WO2014030148 | A2 | 2/2014 |
| WO | WO2014184277 | A1 | 11/2014 |

TUNABLE WHITE LIGHT SOURCE WITH VARIABLE UV COMPONENT

CROSS-REFERENCE TO PRIOR APPLICATIONS

This application is the U.S. National Phase application under 35 U.S.C. § 371 of International Application No. PCT/EP2016/075614, filed on Oct. 25, 2016, which claims the benefit of European Patent Application No. 15193780.2, filed on Nov. 10, 2015. These applications are hereby incorporated by reference herein.

FIELD OF THE INVENTION

The invention relates to a lighting system comprising a plurality of light sources and to a method of illuminating an indoor space.

BACKGROUND OF THE INVENTION

Lighting devices with a plurality of light sources are known in the art. US2012/0032208, for instance, describes a light emission device includes multiple electrically activated solid state emitters (e.g. LEDs) having differing spectral output from one another; and/or phosphor material including one or more phosphors arranged to receive spectral output from at least one of the solid state emitters and to responsively emit a phosphor output, to provide spectral output. In one arrangement, multiple LEDs and multiple phosphors have different peak wavelengths and provide aggregated light output with less than four light emission peaks. In one arrangement, a plot of aggregated output emissions (light intensity versus wavelength) has a nonnegative slope between more than two wavelength peaks. In one arrangement, a light emission device generates a user-perceptible transition in color of light at a predetermined time period as an indicative of a need to perform at least one selected task.

SUMMARY OF THE INVENTION

Artificial white light is being adopted at a high rate. Such light sources can produce high quality light with a CRI beyond 90 with very high efficiencies. However, one of the problems of such light sources as compared with sun light is the absence certain parts of the spectrum which have specific benefits to humans beyond providing visible light.

Hence, it is an aspect of the invention to provide an alternative lighting system, which preferably further at least partly obviates one or more of above-described drawbacks. Especially, it is an aspect of the invention to provide a lighting system that may mimic daylight and have at least part of the beneficial properties of daylight.

It appears that UV light (albeit at very low intensities) is very important for production of vitamin D (or for skin tanning, insect attraction, skin treatment, etc.). For this purpose, it is possible to introduce UV LEDs in combination with white LEDs. White and UV emitting LEDs can be combined to produce light sources for producing Vitamin D.

However, such devices do not necessarily mimic daylight. It appears that it is beneficial for human users to have a color temperature tunable light source imitating day light having more UV component at high color temperatures than at lower color temperatures.

Hence, amongst others we suggest herein using blue and UV light for producing light which can be tuned on the BBL.

In the case of a UV source, in embodiments the UV light may be partially converted to blue or white light with high CCT (correlated color temperature) keeping the Stokes shift losses at a minimum. For instance, blue LEDs can be used to produce white light with low CCT. Herein, we describe various configurations and driving schemes to produce a CCT controllable white light source with variable UV component.

In a first aspect, the invention provides a lighting system comprising a first light source, a second light source and a control system configured to control the first light source and the second light source, wherein the first light source is configured to provide first light source light comprising (i) a UV component for generating light in the wavelength range of 200-380 nm; and (ii) (iia) a blue component or (iib) a blue component and a yellow component; wherein the second light source is configured to provide white second light source light having a second light source light correlated color temperature (Tc2); and wherein the lighting system is configured to provide lighting system light comprising one or more of said first light source light and said second light source light, with the lighting system light having a controllable correlated color temperature (Tc) and having a relatively increased UV content at increasing correlated color temperature; wherein the first light source comprises a UV light source configured to provide UV first light source radiation in the wavelength range of 200-380 nm and a luminescent material configured to convert part of the UV first light source radiation into blue luminescent material light, and wherein the first light source light comprises said blue luminescent material light and said UV first light source radiation, or wherein the first light source comprises a UV light source configured to provide UV first light source radiation in the wavelength range of 200-380 nm and a luminescent material configured to convert part of the UV first light source radiation into blue luminescent material light and configured to convert part of the UV first light source radiation and/or the blue luminescent material light into yellow luminescent material light, and wherein the first light source light comprises said blue luminescent material light, said yellow luminescent material light and said UV first light source radiation.

With such lighting system, it is possible to control the color temperature (herein also indicated as correlate color temperature (Tc)) of the lighting system light and also to provide UV light, which may be beneficial for a human user, with a natural transition from cold light with relative high UV content to warm white with relative low UV content. Such lighting system light can be used for all kind of applications and allows a healthy contribution of UV light, which is presently absent in many indoor lighting. Further, the color temperature variability may also add to the usefulness for humans, as the lighting may with this variability mimic outdoor lighting color temperature variations during the day.

International Publication No. WO 2014/184277 A1 discloses an apparatus for promoting D-vitamin production in a living organism. The apparatus comprising at least one lamp assembly, said at least one lamp assembly is adapted to emit light, wherein the light at least emulates natural or IR light and UV light at wavelengths between 270 nm and 315 nm, wherein the at least one lamp assembly comprises a plurality of LEDs.

International Publication No. WO 2008/125672 A1 discloses an LED light comprising a housing, a plurality of LEDs comprising first LEDs emitting light in a first wavelength range, a drive unit, and a conversion material which for generating light in a conversion wavelength range that is at least partially different from the first wavelength range. The plurality of LEDs further comprise at least second LEDs which emit light in a second wavelength range. The second LEDs can optionally be driven in addition to the first LEDs, the light of the second LEDs being at least partially different from the wavelength range of the first LEDs and additionally exciting the same conversion material to cause the conversion material to emit light resulting in a color shift to more warm white light.

International Publication No. WO 2010/016009 A1 discloses A UV-VIS light emitting system for stimulating vitamin D synthesis, comprising at least a first source emitting within the visible range and at least a second source emitting at least within the UVB range, wherein the light emitting system has a source efficiency of 84 lm/W or larger and a specific spectral power distribution.

International publication WO 2014/030148 A2 discloses a light emitting assembly comprising a first light source emitting light in a Ultra Violet spectral range, a second light source emitting light in a blue spectral range having a first peak wavelength, a first luminescent material being arranged convert light in the Ultra Violet spectral range towards light in the blue spectral range, a second luminescent material being arranged fully convert the received light in the blue spectral range towards light of the red, orange, green or yellow spectral range, and a light exit window being arranged to transfer light emitted by the first luminescent material and by the second luminescent material into an ambient of the light emitting assembly.

Hence, especially in a further aspect the invention also provides a method of illuminating an indoor space, comprising providing with said lighting system said lighting system light in said indoor space. The term space may for instance relate to a (part of) hospitality area, such as a restaurant, a hotel, a clinic, or a hospital, etc. The term "space" may also relate to (a part of) an office, a department store, a warehouse, a cinema, a church, a theatre, a library, etc. However, the term "space" also relate to (a part of) a working space in a vehicle, such as a cabin of a truck, a cabin of an air plane, a cabin of a vessel (ship), a cabin of a car, a cabin of a crane, a cabin of an engineering vehicle like a tractor, etc. The term "space" may also relate to (a part of) a working space, such as an office, a (production) plant, a power plant (like a nuclear power plant, a gas power plant, a coal power plant, etc.), etc. For instance, the term "space" may also relate to a control room, a security room, etc. The invention is thus especially relevant for indoor lighting.

The UV content can be controlled by controlling the relative contribution of the first light source (to the system light).

Optionally, in embodiments in addition to the UV radiation provided by the first light source, a further light source, herein also indicated as "third" light source, may be provided configured to provide additional UV radiation.

However, in other embodiments the UV radiation is substantially exclusively provided via the first light source.

Especially, the lighting system is configured to provide (white) lighting system light having a UV content in the range of 1-20% (Watt/Watt), such as in the range of 2-20%, like 4-18%. The indication "% (Watt/Watt)" indicates the percentage of the total power provided in the range of 200-380 nm provided by the lighting system relative to the total power in the range of 200-780 nm provided by the lighting system. Hence, especially at least 80% of the total power in the range of 200-780 nm is in the visible and especially at least 1% of the total power in the range of 200-780 nm is in the range of 200-380 nm, especially in the range of 280-320 nm (see also below). Especially, the lighting system is configured to provide lighting system light including visible light in (substantially) all possible settings. In yet further embodiments, the lighting system is configured to provide white lighting system light including visible light in (substantially) all possible setting.

Herein, the UV range is indicated as the wavelength range 200-380 nm and the visible range is indicated as the wavelength range 380-780 nm (see also below).

The terms "blue light" or "blue emission" especially relates to light having a wavelength in the range of about 420-495 nm (including some violet and cyan hues). The terms "green light" or "green emission" especially relate to light having a wavelength in the range of about 495-570 nm. The terms "yellow light" or "yellow emission" especially relate to light having a wavelength in the range of about 570-590 nm. The terms "orange light" or "orange emission" especially relate to light having a wavelength in the range of about 590-620 nm. The terms "red light" or "red emission" especially relate to light having a wavelength in the range of about 620-780 nm. The term "pink light" or "pink emission" refers to light having a blue and a red component. The terms "visible", "visible light" or "visible emission" refer to light having a wavelength in the range of about 380-780 nm.

The term white light herein, is known to the person skilled in the art. It especially relates to light having a correlated color temperature (CCT) between about 1500-20000, such as 2000 and 20000 K, especially 2700-20000 K, for general lighting especially in the range of about 2700 K and 6500 K, and especially within about 15 SDCM (standard deviation of color matching) from the BBL (black body locus), especially within about 10 SDCM from the BBL, even more especially within about 5 SDCM from the BBL.

In a specific embodiment, the light source comprises a solid state LED light source (such as a LED or laser diode). Hence, in embodiments the first light source and/or the second light source comprise one or more solid state light sources. The term "light source" may also relate to a plurality of light sources, such as 2-512, such as 2-20 (solid state) LED light sources. Hence, the term LED may also refer to a plurality of LEDs. Therefore, the term "first light source" may also refer to a plurality of (different) first light sources. Likewise, the term "second light source" may also refer to a plurality of (different) second light sources.

The second light source is thus especially configured to provide white light. The second light source may in embodiments comprise two or more light sources that are configured to provide white light. In embodiments, the two or more light sources may be controllable to provide white light or colored light. At least, the second light source includes a setting to provide white light.

The second light source may amongst others be based on an YB-principle or RGB-principle. However, other combinations of colors may also be possible.

The second light source may comprise a blue light source and a yellow luminescent material to provide white light. Hence, in embodiments the second light source comprises a blue light source configured to provide blue second light source radiation and a luminescent material configured to convert part of the blue second light source radiation into yellow luminescent material light, wherein the white second light source light comprises said blue second light source radiation and said yellow luminescent material light. This does not exclude embodiments wherein a further luminescent material and a further light source is applied to further tune the spectral distribution and/or color temperature of the second light source light. The term "luminescent material" may also refer to a plurality of different luminescent materials.

In yet other embodiments, the second light source comprises an RGB light source. In embodiments, this may relate to a second light source comprising a blue light source configured to provide blue second light source radiation and a luminescent material configured to convert part of the blue second light source radiation into green and red luminescent material light, wherein the white second light source light comprises said blue second light source radiation and said green and red luminescent material light. The luminescent material may especially include a combination of different luminescent materials. This does not exclude embodiments wherein a further luminescent material and a further light source is applied to further tune the spectral distribution and/or color temperature of the second light source light.

In alternative embodiments, two or more of the colors of the second light source light are provided by two or more different light sources, such as a combination of blue, green and red LEDs.

Whatever configuration is chosen for the second light source, the second light source is at least able to provide white second light source light. Hence, the second light source is configured to provide said white second light source light. Hence, even when the second light source comprises a plurality of (different) light sources, the control system controls these plurality of (different) light sources to provide second light source light, with at a setting of the lighting system the second light source light being white light.

Especially, the second light source light correlated color temperature (Tc2) is selected from the range of 1500-3500 K, such as 2000-3500 K, like 2500-3500 K, such as especially 2700-3500 K, like equal to or lower than 3000 K. The color temperature of the white light of the second light source may be relatively low. Especially, the lowest color temperature of the lighting system light may essentially be based on the second light source light.

Optionally, the second light source may be configured to provide second light source light also including a UV component. Especially, the first light source and second light source are configured such that when providing white lighting system light, a decrease from the contribution of the second light source light to the total lighting system light leads to an increase in color temperature and to an increase in UV contribution to the total lighting system light.

The first light source is especially configured to provide first light source light comprising (i) a UV component; and one of (iia) a blue component and (iib) a blue component and a yellow component. The first light source may in embodiments comprise two or more light sources that are configured to provide said first light source light. In embodiments, the two or more light sources may be controllable to provide said first light source light. At least, the first light source includes a setting to provide said first light source light. The first light source is thus especially configured to provide at least UV radiation, and optionally light in one or more parts of the visible spectrum, such as in the yellow, or in the green and red, though in embodiments also orange may be included.

Hence, in embodiments the first light source is configured to provide UV radiation and blue light. In other embodiments the first light source is configured to provide UV radiation and blue light and yellow light. Especially, in the latter embodiments the first light source may be configured to provide white light (at a setting of the lighting system; see further also below).

As indicated above, the first light source light includes at least UV radiation (in a setting of the lighting system). Even more especially, in embodiments the UV component has a wavelength selected from the range of 280-320 nm. It appears that especially such radiation may be beneficial for the skin and/or generation of vitamin D. Even more especially, at least 80% of the total power in the wavelength range of 200-400 nm of the lighting system light is in the range of 280-320 nm. Hence, especially the UV radiation or UV component comprises UV-B radiation.

Due to admixing of blue light of the first light source to the second light source light, the color temperature can be increased. Automatically, then also the (relative) UV content is increased. Hence, in embodiments the lighting system is configured to control the color temperature of the lighting system light by admixing of blue light with the white light of the second light source.

In this way, a higher color temperature can be created, especially at least 300 K higher, such as at least 500 K higher, like in the range of 300-3000 K higher.

In yet other embodiments, the first light source is configured to provide white light source light (at a setting of the lighting system). Hence, in further embodiments the first light source is configured to provide white first light source light having a first light source light correlated color temperature (Tc1) of at least 300 K higher than the second light source light correlated color temperature (Tc2), especially at least 500 K higher. Therefore, in embodiments wherein the first light source is configured to provide white first light source light, Tc1>Tc2.

The white light of the first light source may be generated in different way, but especially comprises a blue component and a yellow component.

In embodiments, the first light source comprises a UV light source configured to provide UV first light source radiation and a luminescent material configured to convert part of the UV light source radiation into visible luminescent material light, wherein the (white) first light source light comprises said visible luminescent material light and said UV first light source radiation. This does not exclude embodiments wherein a further luminescent material and a further light source is applied to further tune the spectral distribution and/or color temperature of the second light source light.

As indicated above, the term "luminescent material" may also refer to a plurality of different luminescent materials.

Especially, the visible luminescent material light comprises blue light and even more especially blue light and yellow light, such as to provide white light (with a high correlated color temperature).

In yet another embodiment, the visible luminescent material light comprises blue light, green light and red light.

In yet another embodiment, the visible luminescent material light comprises a blue component and one or more of a green component, a yellow component and a red component. Dependent upon the desired color temperatures or color temperature range, adding one or more of these components may assisting in keeping the color point of the white lighting device light close to the BBL, especially within 15 SDCM from the BBL, such as within 10 SDCM from the BBL, like within about 5 SDCM from the BBL. Hence, the invention also includes a method (as defined herein) comprising providing white lighting system light having a maximum deviation from the black body locus (BBL) of 15 SDCM.

Hence, the first light source comprises a UV light source configured to provide UV light source radiation and a luminescent material configured to convert part of the UV light source radiation into blue luminescent material light, and wherein the first light source light comprises said blue luminescent material light and said UV first light source radiation. Especially in these embodiments, the color temperature of the lighting system light may be tunable by admixing of blue light to the white light of the second light source.

Alternatively, the first light source comprises a UV light source configured to provide UV light source radiation and a luminescent material configured to convert part of the UV light source radiation into blue luminescent material light and configured to convert part of the UV light source radiation and/or the blue luminescent material light into yellow luminescent material light, and wherein the (white) first light source light comprises said blue luminescent material light, said yellow luminescent material light, and said UV first light source radiation. Especially in these embodiments, a plurality of different luminescent materials may be applied. The luminescent material configured to provide yellow light may be configured to absorb the UV radiation and/or the blue radiation, for conversion into yellow luminescent material light. In this way, white first light source light is generated by the first light source.

Hence, in an embodiment the first light source is configured to provide blue light and UV radiation.

In a further embodiment, the first light source is configured to provide blue light, green light, and UV radiation. In yet a further embodiment, the first light source is configured to provide said blue light and said green light using one or more luminescent materials configured to convert light of a UV light source into said blue and green light.

In yet another embodiment, the first light source is configured to provide white light and UV radiation. In yet a further embodiment, the first light source is configured to provide white light using one or more luminescent materials configured to convert light of a UV light source into white light. The first light source will especially in such embodiments be configured to convert part of the UV light source light into visible luminescent material light and further provide (part of) the remaining UV as UV radiation (i.e. UV component).

In embodiments, the first light source and the second light source have fixed color points, respectively. In yet other embodiments, the first light source has a fixed color point and the second light source has a tunable color point. In yet further embodiments, both light sources have tunable color points, respectively. However, especially the first light source is configured to provide substantially only UV radiation or has a fixed color point (and also provides UV radiation, but UV radiation does not contribute to the color point of the light source light).

Notwithstanding the above, the lighting system may further comprise a third light source configured to provide third light source light having a UV component or a red component. The term "third light source" may also refer to a plurality of (different) light sources. When different light sources are applied, e.g. one or more of these may be configured to provide UV radiation and/or one or more of these may be configured to provide red light.

The lighting system is especially configured to provide lighting system light (including UV radiation). This light may escape form a light exit window. Upstream from such window the light sources are arranged, and downstream from the window a user may perceive the lighting system light. Hence, in embodiments the lighting system further comprises a light exit window, wherein the lighting system is configured to generate said first light source light and said second light source light upstream from said light exit window and configured to provide said lighting system light downstream from said light exit window.

The terms "upstream" and "downstream" relate to an arrangement of items or features relative to the propagation of the light from a light generating means (here the especially the first light source), wherein relative to a first position within a beam of light from the light generating means, a second position in the beam of light closer to the light generating means is "upstream", and a third position within the beam of light further away from the light generating means is "downstream".

The lighting system is especially configured to provide a plurality of settings, each providing white lighting system light but having different correlated color temperatures. However, the lighting system may optionally also be configured to provide (additional) settings wherein colored light is provided. This may especially be the case when the second light source comprises a plurality of light sources, such as RGB light sources, configured to provide different colors, which at one or more settings may provide white light having the second light source light correlated color temperature, but which at one or more other settings may provide colored light.

The plurality of settings may especially be provided by the control system, configured to control the lighting system light (by controlling the light sources). Therefore, the lighting system further comprises a control system configured to control the power provided to the (one or more) (solid state) light sources. Alternatively or additionally, the control system may be (configured) external from the lighting system. Optionally, the control system may comprise a plurality of elements, of which some may be comprised by the lighting system and others may be external from the lighting system (such as a remote user interface, see also below). The lighting system may e.g. be integrated in an integrated lighting system with a plurality of lighting systems (as described herein) and optional other types of lighting systems than described herein.

In yet a further specific embodiment, the control system is configured to control the power provided to the one or more (solid state) light sources as function of an input signal of a user interface. This user interface may be integrated in the lighting system, but may also be remote from the lighting system. Hence, the user interface may in embodiments be integrated in the lighting system but may in other embodiments be separate from the lighting system. The user interface may e.g. be a graphical user interface. Further, the user interface may be provided by an App, e.g. for a Smartphone or other type of android system. Therefore, the invention also provides a computer program product, optionally implemented on a record carrier (storage medium), which when run on a computer executes the method as described herein (see below) and/or can control (the color temperature of the lighting system light of) the lighting system as described herein (as function of the power provided to the one or more (solid state) light sources).

Alternatively or additionally, the control system is configured to control the power provided to the one or more (solid state) light sources as function of one or more of a sensor signal and a timer. To this end, e.g. a timer and/or a sensor may be used. For instance, the timer may be used to switch off after a predetermined time. Further, for instance the sensor may be a motion sensor, configured to sense motion, with the control system configured to switch on the lighting system when the motion sensor senses motion or presence of e.g. a person. Further, the sensor may be an optical sensor, e.g. to sense the light, especially the lighting system light and/or daylight. In an embodiment, the lighting system is a luminaire. In yet another embodiment the lighting system is a lighting device. In yet a further embodiment, the lighting system is a lighting engine. Further, the lighting system may be part of a device, luminaire or lighting engine.

Hence, in a further aspect the invention also provides an integrated lighting system comprising the lighting system as defined herein and a control system configured to control the lighting system. As indicated above, the control system may also be comprised by the (integrated) lighting system. The integrated lighting system may especially comprise a control system configured to control the lighting system and one or more other systems, such as a plurality of the lighting systems as described herein and optionally also other lighting systems. The control system may control the integrated lighting system(s) as function of one or more of a sensor signal and a timer (see also above).

The lighting system may be part of or may be applied in e.g. office lighting systems, household application systems, shop lighting systems, home lighting systems, accent lighting systems, spot lighting systems, theater lighting systems, warning sign systems, medical lighting application systems, indicator sign systems, decorative lighting systems, portable systems, automotive applications, etc.

BRIEF DESCRIPTION OF THE DRAWINGS

Embodiments of the invention will now be described, by way of example only, with reference to the accompanying schematic drawings in which corresponding reference symbols indicate corresponding parts, and in which.

The schematic drawings are not necessarily on scale.

DETAILED DESCRIPTION OF THE EMBODIMENTS

Figure 1:
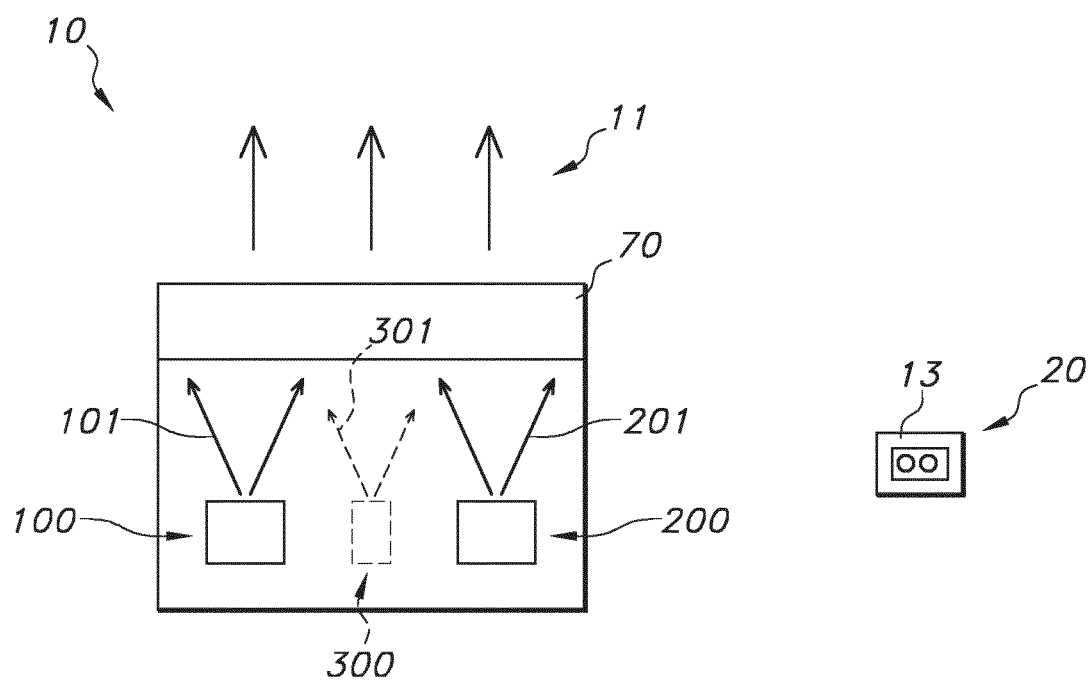
FIG. 1 schematically depicts an embodiment of a lighting system.

FIG. 1 schematically depicts an embodiment of a lighting system, indicated with reference 10. The lighting system 10 comprises a first light source 100, a second light source 200 and a control system 20 configured to control the first light source 100 and the second light source 200. The first light source 100 is configured to provide first light source light 101. The first light source light 101 comprises (i) a UV component, and (ii) (iia) a blue component or (iib) a blue component and a yellow component. The latter variant may provide white light (with a first light source light correlated color temperature Tc2). The second light source 200 is configured to white second light source light 201 having a second light source light correlated color temperature Tc2. Further, the lighting system 10 is configured to provide lighting system light 11 comprising one or more of said first light source light 101 and said second light source light 201, with the lighting system light 11 having a controllable correlated color temperature Tc.

Optionally, the lighting system 10 may further comprising a third light source 300 configured to provide third light source light 301 having a UV component or a red component, though other visible components are not necessarily excluded. This may be used to further tune the spectral distribution of the lighting system light. The third light source is especially also controlled by the control system 20. Reference 13 schematically indicates a user interface.

Especially, the lighting system 10 may further comprise a light exit window 70, wherein the lighting system is configured to generate said first light source light 101 and said second light source light 201 upstream from said light exit window 70 and configured to provide said lighting system light 11 downstream from said light exit window 70. Downstream from the light exit window, the lighting system light 11 is found, which may comprise one or more of the first light source light 101 and second light source light 201.

The lighting system may include further optics, like refractive components such as collimators or lenses, diffractive components such as gratings, reflective components such as diffuse or specular reflectors, optical filters, etc. etc., which are for the sake of clarity not been drawn, but which may be comprised by the lighting system.

Figure 2A:
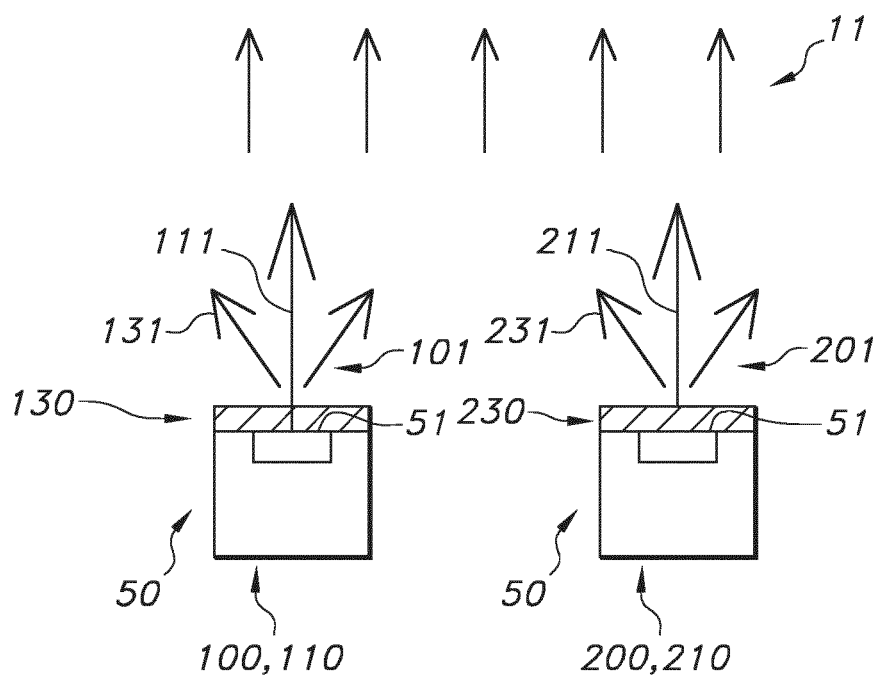
FIGS. 2*a*-2*b* schematically depict some variants of the light sources of the lighting system.
Figure 2B:
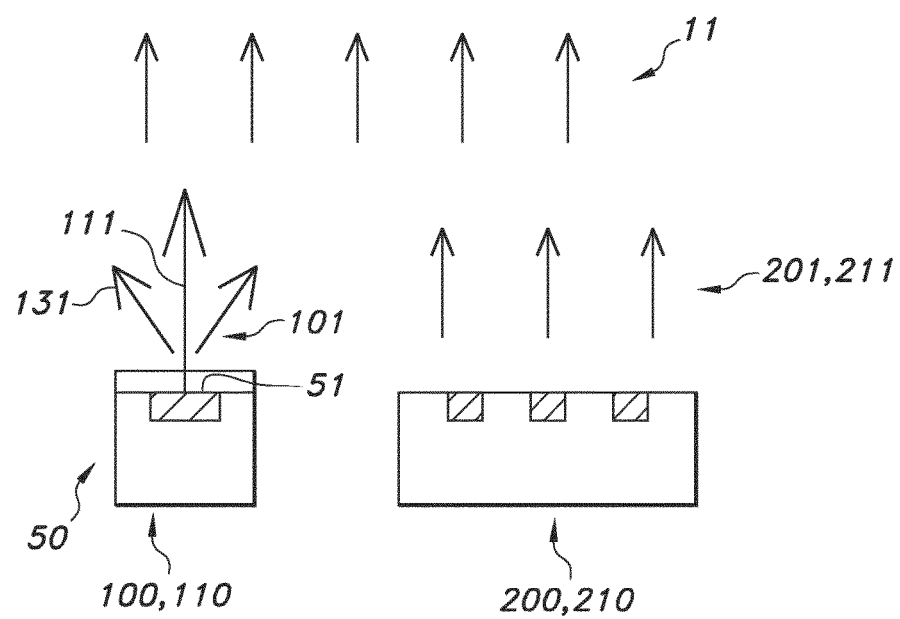

FIGS. 2*a*-2*b* schematically depict some variants of the light sources of the lighting system.

For instance, FIG. 2*a* may schematically depict an embodiment wherein the first light source 100 is configured to provide white first light source light 101 having a first light source light correlated color temperature Tc1 of at least 300 K higher than the second light source light correlated color temperature Tc2.

Such embodiment may e.g. be obtained when the first light source 100 comprises a UV light source 110 configured to provide UV first light source radiation 111 and a luminescent material 130 configured to convert part of the UV light source radiation 111 into visible luminescent material light 131, wherein the white first light source light 101 comprises said visible luminescent material light 131 and said UV first light source radiation 111. The visible luminescent material light may further comprise a yellow component, and alternatively or additionally red and green components of the light generated by the luminescent material. The luminescent material 130 may thus especially include a plurality of different luminescent materials, such as one or more configured to provide blue light and one or more configured to provide yellow light and/or one or more configured to provide green and red light. Other options are however also possible.

In the schematically depicted embodiment of FIG. 2*a*, the second light source 200 may comprise a blue light source 210 configured to provide blue second light source radiation 211 and a luminescent material 230 configured to convert part of the blue second light source radiation 211 into yellow luminescent material light 231, wherein the white second light source light 201 comprises said blue second light source radiation 211 and said yellow luminescent material light 231. In yet other embodiments, the second light source 200 comprises an RGB light source. In embodiments, this may relate to a second light source 200 comprising a blue light source 210 configured to provide blue second light source radiation 211 and a luminescent material 230 configured to convert part of the blue second light source radiation 211 into green and red luminescent material light 231, wherein the white second light source light 201 comprises said blue second light source radiation and said green and red luminescent material light 231. The luminescent material 230 may especially include a combination of different luminescent materials. This does not exclude embodiments wherein a further luminescent material and a further light source is applied to further tune the spectral distribution and/or color temperature of the second light source light 200.

Reference 50 indicates a solid state light source. Reference 51 indicates a LED die. Especially, the first light source 100 and the second light source 200 comprise solid state light sources. Further, especially the first light source 100 comprises a luminescent material. The luminescent material(s) may be in physical contact with the (respective) LED die(s).

The light source and the luminescent materials are especially radiationally coupled. The term "radiationally coupled" especially means that the light source and the luminescent material are associated with each other so that at least part of the radiation emitted by the light source is received by the luminescent material and at least partly converted into luminescence.

The term "luminescent material" herein especially relates to inorganic luminescent materials, which are also sometimes indicated as phosphors. These terms are known to the person skilled in the art.

Alternatively, as schematically depicted in FIG. 2b, the second light source 200 comprises an RGB light source 210, which is not based on luminescent materials. For instance, an RGB LED may be applied.

Note that both FIGS. 2a and 2b may also refer to embodiments, wherein the first light source 100 is configured to provide first light source light 101 comprising a UV component and substantially only a blue component. In such embodiments, the luminescent material 130 may be configured to convert part of the first light source radiation 101 into blue luminescent material light 131. Therefore, in FIGS. 2a and 2b, optionally the first light source 100 comprises a UV light source 110 configured to provide UV light source radiation 111 and a luminescent material 130 configured to convert part of the UV light source radiation 111 into blue luminescent material light 131, and wherein the first light source light 101 comprises said blue luminescent material light 131 and said UV first light source radiation 111.

References 131 and 231 are used to indicate the respective luminescent materials light/radiation, irrespective of their spectral distribution.

Figure 3:
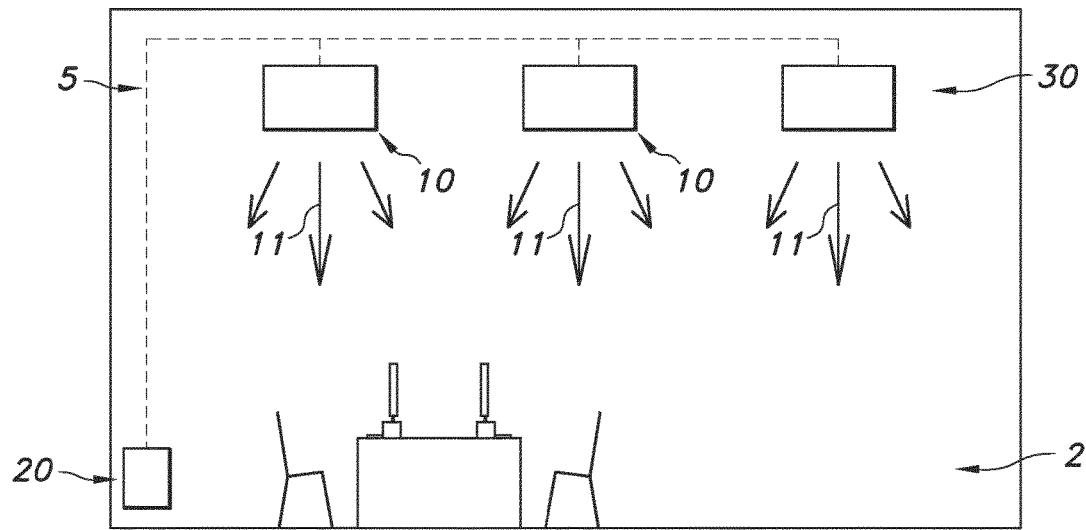
FIG. 3 schematically depicts an integrated lighting system comprising a plurality of lighting systems and a control system.

FIG. 3 schematically depicts an integrated lighting system 5 comprising a plurality of lighting systems 10 and a control system 20. Here, by way of example the integrated lighting system 5 further comprises a lighting system 30 different from the lighting system 10 as defined herein. The lighting system(s) 10 and/or the integrated lighting system 5 may be used to illuminate an indoor space 2, such as an office.

Figure 4:
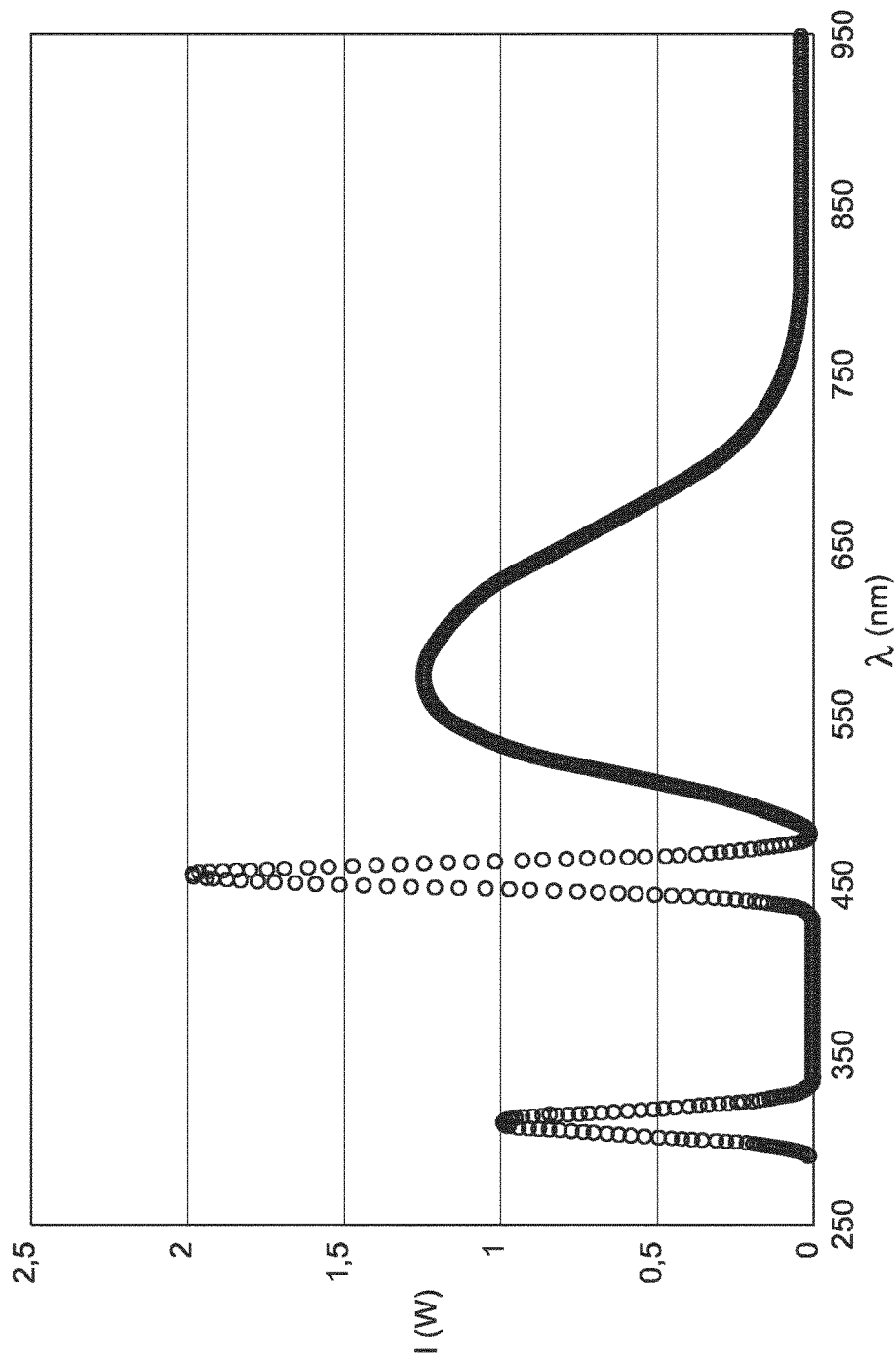
FIG. 4 shows an example spectrum of light of a first light source.

FIG. 4 shows a spectrum of a first light source. Here, a spectrum of white first light source light with blue and yellow is displayed, providing white light. Further, the UV component is displayed. Combining this light with the light of a second light source for providing white light with a lower color temperature may provides white light with a tunable color temperature and a variable UV contribution, which increases with increasing first light source light contribution.

The term "substantially" herein, such as in "substantially all light" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A lighting system comprising a first light source, a second light source and a control system configured to control the first light source and the second light source, wherein:

the first light source is configured to provide first light source light comprising:
a UV component; and
a blue component or a blue component and a yellow component;

the second light source is configured to provide white second light source light having a second light source light correlated color temperature;

the lighting system is configured to provide lighting system light comprising one or more of said first light source light and said second light source light, wherein the lighting system light has a controllable correlated color temperature and a relatively increased UV content with an increased correlated color temperature, wherein the first light source comprises a UV light source configured to provide UV first light source radiation in a wavelength range of 200-380 nm and a luminescent material configured to convert part of the UV first light source radiation into blue luminescent material light, and wherein the first light source light comprises said blue luminescent material light and said UV first light source radiation, or wherein the first light source comprises a UV light source configured to provide UV first light source radiation in the wavelength range of 200-380 nm and a luminescent material configured to convert part of the UV first light source radiation into blue luminescent material light and configured to convert part of the UV first light source radiation and/or the blue luminescent material light into yellow luminescent material light, and wherein the first light source light comprises said blue luminescent material light, said yellow luminescent material light and said UV first light source radiation.

2. The lighting system according to claim 1, wherein the lighting system is configured to provide lighting system light having a UV content, defined by a percentage of the total power provided in the range of 200-380 nm provided by the lighting system relative to a total power in a range of 200-780 nm provided by the lighting system, in a range of 1-20% (Watt/Watt).

3. The lighting system according to claim 1, wherein the second light source light correlated color temperature is selected from a range of 2000-3500 K.

4. The lighting system according to claim 1, wherein the UV component has a wavelength selected from a range of 280-320 nm.

5. The lighting system according to claim 4, wherein at least 80% of the total power in the wavelength range of 200-400 nm of the lighting system light is in the range of 280-320 nm.

6. The lighting system according to claim 1, wherein the first light source and second light source comprise one or more solid state light sources.

7. The lighting system according to claim 1, wherein the second light source comprises a blue light source configured to provide blue second light source radiation and a luminescent material configured to convert part of the blue second light source radiation into yellow luminescent material light, wherein the white second light source light comprises said blue second light source radiation and said yellow luminescent material light.

8. The lighting system according to claim 1, wherein the second light source comprises an RGB light source.

9. The lighting system according to claim 1, wherein the first light source is configured to provide white first light source light having a first light source light correlated color temperature of at least 300 K higher than the second light source light correlated color temperature.

10. The lighting system according to claim 1, further comprising a third light source configured to provide third light source light having a UV component or a red component.

11. The lighting system according to claim 1, further comprising a light exit window, wherein the lighting system is configured to generate said first light source light and said second light source light upstream from said light exit window and configured to provide said lighting system light downstream from said light exit window.

12. A method of illuminating an indoor space, comprising providing with the lighting system according to claim 1, said lighting system light in said indoor space.

13. The method according to claim 12, comprising providing white lighting system light having a maximum deviation from a black body locus of 15 SDCM.

* * * * *